United States Patent [19]

Katsuragi

[11] Patent Number: 5,101,826
[45] Date of Patent: Apr. 7, 1992

[54] NONCONTACT TYPE TONOMETER
[75] Inventor: Kenjiro Katsuragi, Tokyo, Japan
[73] Assignee: Kabushiki Kaisha Topcon, Tokyo, Japan
[21] Appl. No.: 758,204
[22] Filed: Sep. 12, 1991

Related U.S. Application Data

[63] Continuation of Ser. No. 346,759, May 2, 1989, abandoned.

[30] Foreign Application Priority Data

May 11, 1988 [JP] Japan .................... 63-114082

[51] Int. Cl.⁵ .............................................. A61B 3/16
[52] U.S. Cl. ..................................... 128/645; 351/208
[58] Field of Search ................................ 128/645-652;
351/208, 211, 212, 213, 216

[56] References Cited

U.S. PATENT DOCUMENTS 3,756,073 9/1973 Lavallee et al. ..................... 128/648
4,665,923 5/1987 Kobayashi ............................ 128/648

Primary Examiner—Lee S. Cohen
Assistant Examiner—John P. Lacyk
Attorney, Agent, or Firm—Finnegan, Henderson, Farabow, Garrett & Dunner

[57] ABSTRACT

A noncontact type tonometer has a nozzle for discharging fluid toward an eye to be tested, an alignment target projecting optical system for projecting an alignment target light used for aligning the eye and an apparatus body toward the center of curvature of the cornea of the eye from the axial direction of said nozzle while converging the same thereto by an objective lens and forming a virtual image at the center of curvature of the cornea, and an alignment light receiving optical system for reimaging the virtual image on a light receiving portion as a target image. The improvement is characterized in that the alignment light receiving optical system is provided with a light splitter adapted to split an alignment target light for forming the virtual image based on specular reflection of the cornea and guiding the same to the light receiving portion in order to verify the alignment with reference to coincidence or noncoincidence of the alignment target image.

10 Claims, 5 Drawing Sheets

NONCONTACT TYPE TONOMETER

This application is a continuation, of application Ser. No. 07/346,759, filed May 2, 1989 now abandoned.

FIELD OF THE INVENTION

This invention relates to an improvement of a noncontact type tonometer, in which the intraocular pressure of an eye to be tested is measured by projecting fluid toward the cornea of the eye and transfiguring it.

BACKGROUND OF THE INVENTION

Heretofore, in noncontact type tonometers, as alignment verification, the vertical and horizontal positions of optical systems of an apparatus body were verified with respect to the eye and the working distance between the eye and a nozzle for discharging fluid toward the eye was verified. In conventional the noncontact type tonometers, an alignment target light may be projected toward the eye from the axial direction of the nozzle in order to verify the alignment. Noncontact type tonometers of this type are designed such that upon verification of the alignment, fluid, such as air pulse or the like, is discharged from the nozzle to transfigure the cornea of the eye and measure the intraocular pressure thereof. (e.g., Japanese Patent Publication No. Sho 56-6772).

However, in conventional noncontact type tonometers of this type, an alignment target light, when the alignment is proper, is made incident to the cornea of the eye from the perpendicular direction as if the alignment target light is converged to the center of curvature of the cornea to form a virtual image. The virtual image is reimaged on a reticle plate, and then the alignment is determined from the sharpness of the reimaged virtual image and from the position tonometers of the virtual image on the reticle plate. In conventional it is difficult to determine correctly and rapidly if proper alignment exists.

Also, it is designed as such that the anterior portion of the eye cannot be observed. Accordingly, the inspector of the eye has no way to recognize the state of the eye during the period of time from the aligning operation till the fluid discharge and thus inconvenient. For example, if the discharge of fluid takes place when the lid of the eye to be tested is closed, the obtained value of the intraocular pressure becomes unreliable.

SUMMARY OF THE INVENTION

It is therefore the object of the present invention to provide a noncontact type tonometer, in which the alignment can be verified correctly and rapidly, and in which reliability of the intraocular pressure measurement can be improved.

In order to achieve the above object, a noncontact type tonometer according to the present invention includes a nozzle for discharging fluid toward an eye to be tested;

an alignment target projecting optical system for projecting an alignment target light used for aligning the eye and an apparatus body toward the center of curvature of the cornea of the eye from the axial direction of the nozzle while converging the same thereto by an objective lens and forming a virtual image at the center of curvature of the cornea; and an alignment light receiving optical system for reimaging the virtual image on a light receiving portion as a target image;

the improvement is characterized in that said alignment light receiving optical system is provided with a light splitter adapted to split an alignment target light for forming said virtual image based on specular reflection of the cornea and guiding the same to said light receiving portion in order to verify the alignment with reference to coincidence or noncoincidence of the alignment target image.

A noncontact type tonometer according to a second embodiment of the present invention further includes an illuminating light source for illuminating the anterior portion of the eye and an observing optical system for observing the anterior portion.

A noncontact type tonometer according to the present invention is of the type wherein an alignment target light, when the alignment is proper, is made incident to the cornea of the eye from the perpendicular direction so that the alignment target light is converged to the center of curvature of the cornea to form a virtual image at the center of curvature of the cornea. The alignment is verified by the separation and the subsequent coincidence of a plurality of alignment target images. Therefore, the alignment can be verified correctly and rapidly. Moreover, reliability of the intraocular pressure measurement can be improved.

Also, the inspector can recognize the state of the eye during the period of time from the alignment operation till the discharging of fluid.

BRIEF DESCRIPTION OF THE DRAWINGS

FIG. 1 and FIG. 2 are views showing an optical system of the first embodiment;

FIG. 3 is a plan view of a filter shown in FIG. 1;

FIG. 4 is a schematic view showing the image of an anterior portion of an eye to be tested and an alignment target image formed on a CCD when a reduction lens shown in FIG. 1 is inserted;

FIG. 5 is a schematic view showing the image of the anterior portion and the alignment target image formed on a CCD when the reduction lens shown in FIG. 1 is not inserted;

FIG. 6 is a schematic view for explaining the function of the reduction lens shown in FIG. 1;

FIG. 7 is a schematic view for explaining the inconvenience of the first embodiment; and FIG. 8 is a view showing an optical system of the second embodiment.

DESCRIPTION OF THE PREFERRED EMBODIMENT

The embodiments of a noncontact type tonometer according to the .present invention will be described hereunder with reference to the accompanying drawings.

FIG. 1 through FIG. 4 are illustrations showing a first embodiment of a noncontact type tonometer of the present invention.

Figure 1:
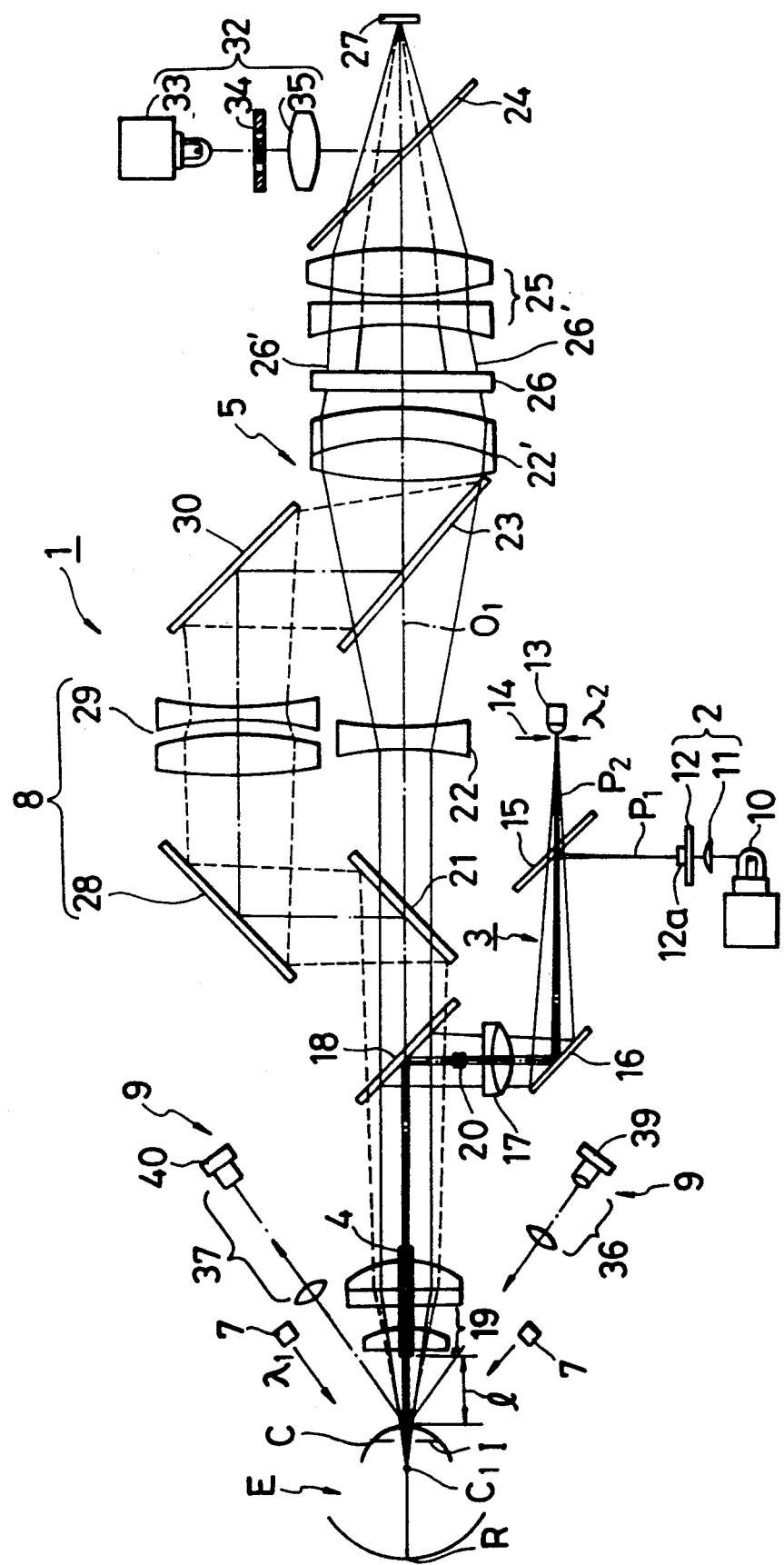
FIG. 1 through FIG. 6 show a first embodiment of a non-contact type tonometer according to the present invention.

In FIG. 1, 1 denotes an optical system of a noncontact type tonometer, E denotes an eye to be tested, C denotes the cornea of the eye, and R denotes the retina of the eye. The optical system 1 includes a fixation mark projecting optical system 2, an alignment target projecting optical system 3, a nozzle 4, an alignment light receiving optical system 5, a reticle image projecting optical system 32, an illuminating light source 7 for illuminating the anterior portion of the eye E, and observing optical system 8, and a cornea applanation detecting optical system 9.

The fixation mark projecting optical system 2 generally comprises a visible light source 10, a condenser lens 11, and a fixation mark plate 12. 12a denotes a fixation mark. The fixation mark plate 12 is illuminated by the visible light source 10 to emit a fixation mark light $P_1$. The alignment target mark projecting optical system 3 generally comprises an infrared light emitting diode 13, a diaphragm 14, a dichroic mirror 15, a total reflection mirror 16, a collimator lens 17, a half mirror 18, and an objective lens 19. The dichroic mirror 15, the total reflection mirror 16, the collimator lens 17, the half mirror 18, and the objective lens 19 are also commonly used as the fixation mark projecting optical system 2 in this embodiment. The dichroic mirror 15 permits an infrared light to be transmitted therethrough and to reflect a visible light. Also, the dichroic mirror 18 has such function as to reflect a visible light and to permit an infrared light to be partly transmitted therethrough.

A fixation mark light $P_1$ is reflected by the dichroic mirror 15 in such a manner as to be coaxial with the optical axis of the alignment target projecting optical system 3 and is reflected by the total reflection mirror 16 and guided to the collimator lens 17. The fixation mark light $P_1$ is collimated by the collimator lens 17. The collimated fixation mark light $P_1$ is reflected by the dichroic mirror 18 and is projected onto the retina R of the eye E through the nozzle 4. The patient gazes at the fixation mark light $P_1$. In case the patient suffers from myopia or hyperopia, a diopter correcting lens 20 may be inserted in an optical path. By this, the patient sees the fixation mark 12a clearly, any external correction. The axis of the nozzle 4 is coaxial with the optical axis $O_1$ of the alignment target light receiving optical system 5.

The alignment target projecting optical system 3 projects an alignment target light $P_2$ toward the center $C_1$ of curvature of the cornea of the eye E from the axial direction of the nozzle 4 while converging it by the objective lens 19. The alignment target light $P_2$ is transmitted through the dichroic mirror 15, reflected by the total reflection mirror 16 and guided to the collimator lens 17 so as to be collimated. The collimated alignment target light $P_2$ is reflected by the dichroic mirror 18 and is guided to the objective lens 19. When the alignment is proper, the alignment target light $P_2$ is made incident to the cornea C from the perpendicular direction such that the light $P_2$ is converged to the center $C_1$ of curvature of the cornea. And, the alignment target image $P_2$ is reflected on the outer surface of the cornea C. By this, a virtual image is formed at the center $C_1$ of curvature of the cornea C based on the alignment target light $P_2$.

The objective lens 19 is commonly used in the alignment light receiving optical system 5 and the observing optical system 8. The alignment target light receiving optical system 5 includes a dichroic mirror 21, an alignment enlarging projecting lens 22, two a lens 22', dichroic mirrors 23 and 24, a reduction lens 25, and a filter 26 in addition to the objective lens 19. The dichroic mirrors 21 and 23 reflect an infrared light of a wavelength $\lambda_1$ and permit an infrared light of a wavelength $\lambda_2$ to transmit therethrough. The infrared light of the wavelength $\lambda_2$ is used as the alignment target light $P_2$. The infrared light of the wavelength $\lambda_1$ is used as an illuminating light for illuminating the anterior portion of the eye E (including the iris I).

The alignment target light $P_2$ for forming a virtual image at the center $C_1$ of curvature of the cornea C based on specular reflection of the cornea C is made into a parallel pencil of rays by the objective lens 19. And, this alignment target light $P_2$ is transmitted through the dichroic mirrors 18 and guided to the alignment enlarging projecting lens 22. The alignment target light $P_2$ is enlarged by the alignment enlarging projecting lens 22, transmitted through the dichroic mirror 23 and the lens 22' and guided to the filter 26.

Figure 3:
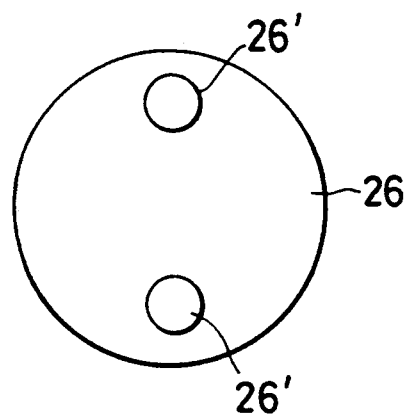

The filter 26 includes circular transmitting areas represented by 26 symmetrical with each other with respect to the center. As shown in FIG. 3, two circular transmitting areas 26' are disclosed. These circular transmitting areas, 26' are optically transparent with respect to the infrared light of the wavelength $\lambda_2$ and optically opaque with respect to the infrared light of the wavelength $\lambda_1$. The remaining area of the filter 26 is optically transparent with respect to the infrared light of the wavelength $\lambda_1$ and optically opaque with respect to the infrared light of the wavelength $\lambda_2$. The dichroic mirror 24 is of the type for reflecting visible light and permitting an infrared light to transmit therethrough.

Therefore, when the alignment is proper, the alignment target light $P_2$ is split into a symmetrical bundle of rays with respect to the optical axis $O_1$ and imaged on a CCD 27 as a light receiving portion. That is, the filter 26 functions as a light splitter which splits the alignment target light for forming a virtual image based on the specular reflection of the cornea and guides it to the light receiving portion.

The observing optical system 8 includes a total reflection mirror 28, an anterior portion projecting lens 29, and a total reflection mirror 30. The illuminating light is incident on the anterior portion and is reflected therefrom. The reflected light is transmitted to the objective lens 19 and the dichroic mirror 18. The reflected light transmitted through the dichroic mirror 18 is reflected toward the total reflection mirror 28 by the dichroic mirror 21 and branched from the optical path of the alignment light receiving optical system 5. The reflected light is guided to the filter 26 through the anterior portion projecting lens 29, the total reflection mirror 30, the dichroic mirror 23 and the lens 22'. And, the reflected light is transmitted to the remaining area of the filter 26 and reaches the reduction lens 25.

Figure 6:
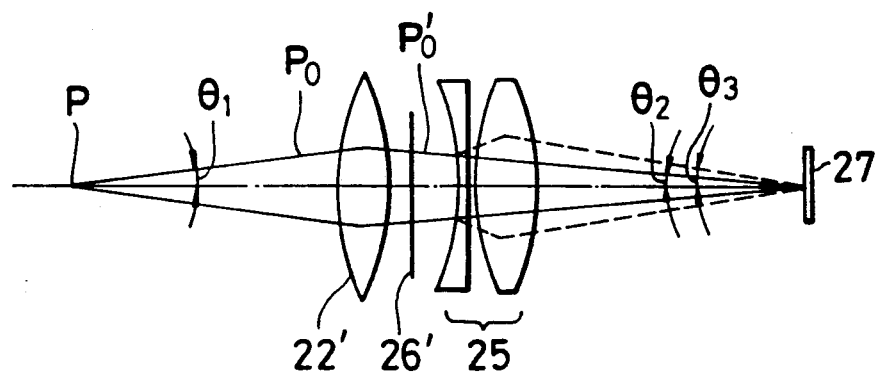

The reduction lens 26 is inserted between the filter 25 and the dichroic mirror 24 when the working distance l from the apex of the cornea C to the nozzle 4 is roughly adjusted. As is schematically shown in FIG. 6, a ray of light $P_0$ is emitted from one point P of the anterior portion at angle $\theta_1$. This ray of light $P_0$ becomes a ray of light $P_0'$ which is converged toward the CCD 27 by the lens 22'. This ray of light $P_0'$ is made incident to the CCD 27 at angle $\theta_2$ when the reduction lens 25 is not inserted in the optical path of the alignment light receiving optical system 5. Also, the ray of light $P_0'$ is made incident to the CCD 27 at angle $\theta_3$ when the reduction lens 25 is inserted in the optical path of the alignment light receiving optical system 5. Therefore, the angular power is set to $r_1 = \theta_1/\theta_2$ when the reduction lens 25 is not inserted in the optical path of the alignment optical system 5 and the angular power is set to $r_2 = \theta_1/\theta_3$ when the reduction lens 25 is inserted in the optical path of the alignment optical system 5. When the reduction lens 25 is inserted in the optical path of the alignment optical system 5, since the angle $\theta_3$ of the ray of light Po' becomes larger than the angle $\theta_2$ when the reduction lens 25 is not inserted in the optical path of the alignment optical system 5, it becomes $r_1 > r_2$. Thus, the power becomes low when the reduction lens 25 is inserted.

Figure 4:
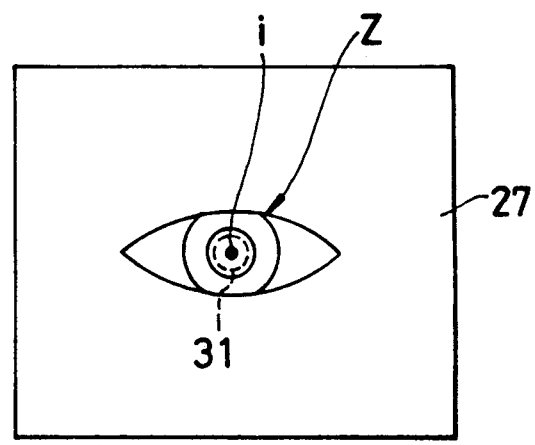

Therefore, when the reduction lens 25 is inserted, the entire anterior portion image Z is formed in the CCD 27 in its reduced scale as shown in FIG. 4. In case that the working distance 1 is not proper here, since the alignment target image i formed by the symmetrical bundles of light becomes vague and separated, the inspector can roughly adjust the working distance 1 by moving the apparatus body along and the optical axis $O_1$ with reference to the anterior portion image Z. Also, in the case that the optical axis $O_1$ is greatly displaced in the vertical and horizontal directions with respect to the eye E, the inspector may adjust the alignment by moving the apparatus body in the vertical and/or horizontal direction. The judgement whether the optical axis $O_1$ is displaced in the vertical and horizontal directions with respect to the eye E is made with reference to a reticle circle 31 formed in the CCD 27. This reticle circle 31 is formed by a reticle image projecting optical system 32. The reticle image projecting optical system 32 generally comprises a visible light source 33, a reticle target 34, and a projecting lens 35.

Figure 2:
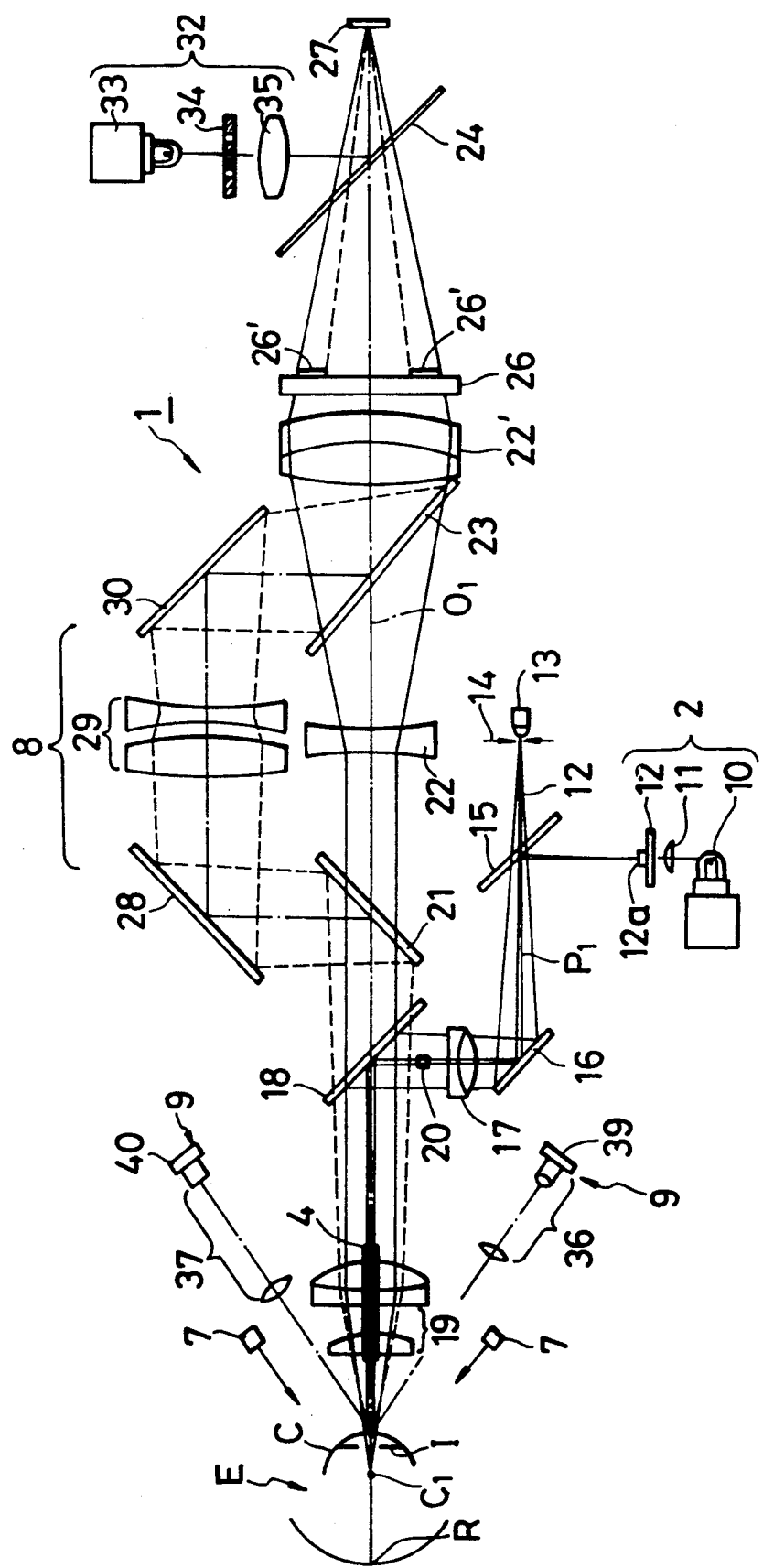
Figure 5:
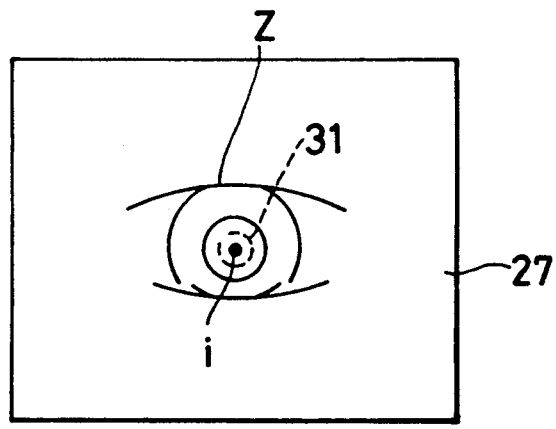

On the other hand, when a fine adjustment is carried out, the reduction lens 25 is removed from the optical path of the alignment light receiving optical system 5 as shown in FIG. 2. Then, the anterior portion image Z is formed in the CCD 27 in relatively enlarged scale with respect to the reticle circle 31. Therefore, the vertical and horizontal displacement of the alignment target image, which appeared to the inspector to be located at the center when the rough adjustment is carried out, can be confirmed according to the relative positional relationship between the reticle circle 31 and the anterior portion image as shown in FIG. 5.

The corneal applanation detecting optical system 9 comprises a detecting light projecting optical system 36, and a detecting light receiving optical system 37. 39 denotes a light projector and 40 denotes a light receiver. The wavelength of the detecting light is $\lambda_2$. When this detecting light is being emitted, irradiation of the alignment light $P_2$ toward the E is stopped.

Figure 7:
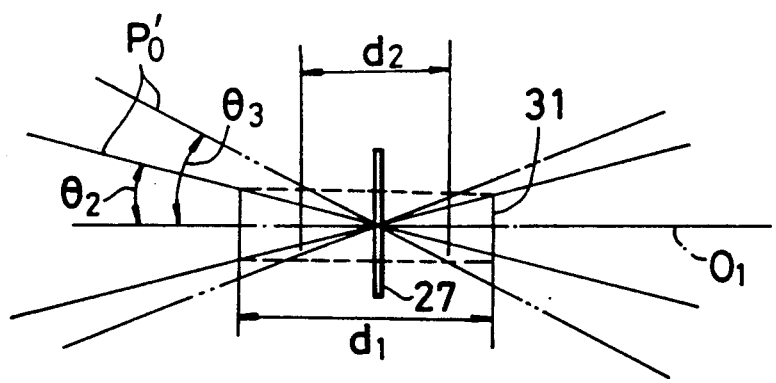
FIG. 7 and FIG. 8 show a second embodiment of a noncontact type tonometer according to the present invention.
Figure 8:
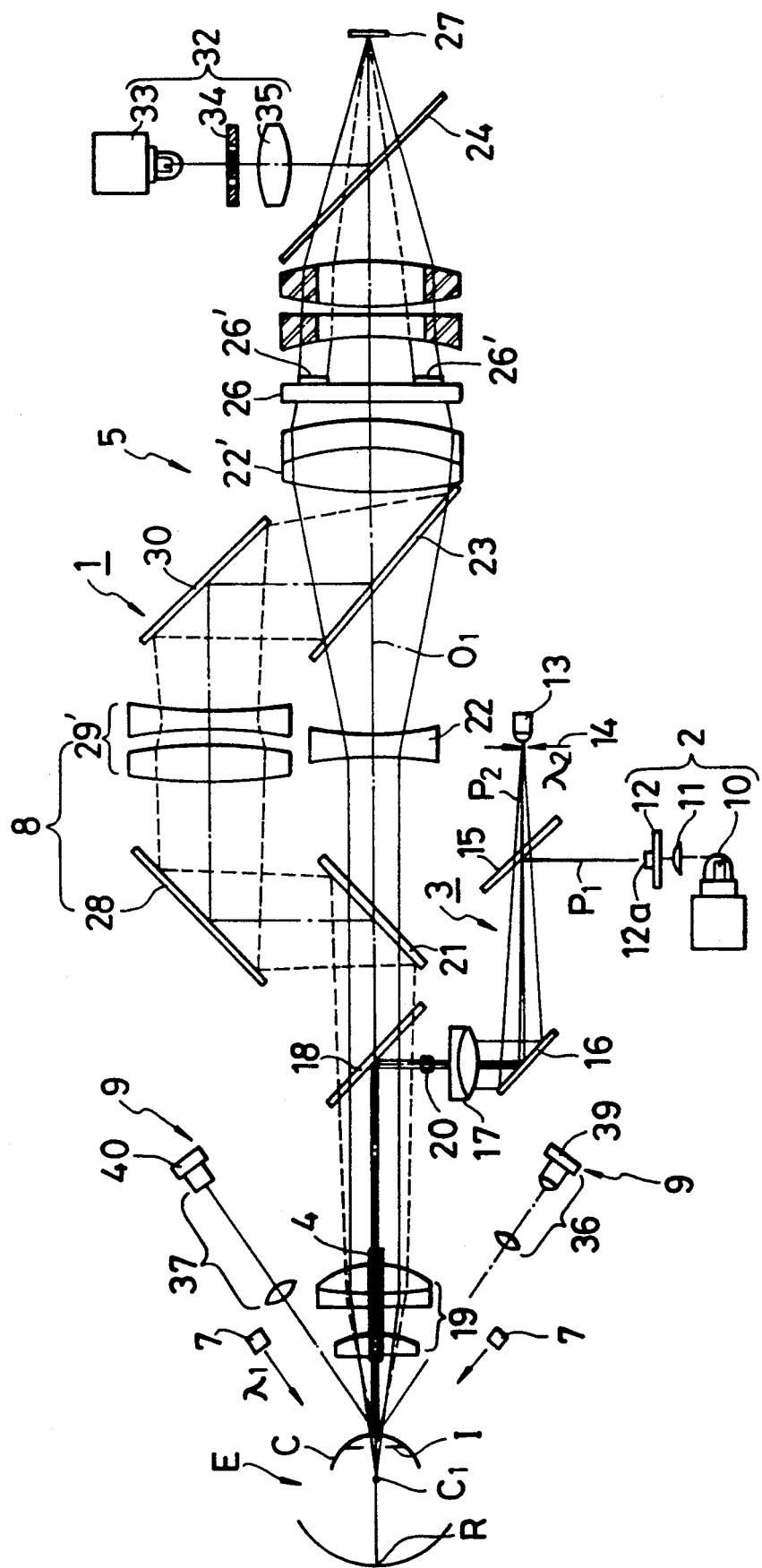

FIG. 7 and FIG. 8 show a second embodiment of a noncontact type tonometer according to the present invention.

As is shown in FIG. 7, in the first embodiment, when the reduction lens 25 is inserted in the alignment optical system 5, the angle $\theta_3$ of the ray of light Po' becomes larger than the angle $\theta_2$ of the ray of light Po when the reduction lens 25 is not inserted therein. Therefore, when reviewing the case where the alignment is adjusted in the direction of the optical axis $O_1$, the moving range $d_2$ with respect to the reticle circle 31 becomes smaller when the reduction lens 25 is inserted in the alignment optical system 5 compared with the moving range $d_1$ with respect to the reticle circle 31 when the reduction lens 25 is not inserted in the alignment optical system 5, and sensitivity of conformity and nonconformity of the alignment target image i becomes high when in low power. If possible, however, sensitivity of conformity and nonconformity of the alignment target image i is desirably raised when the anterior portion image Z is enlarged.

FIG. 8 is a schematic view of an optical system satisfying the above requirements. When an anterior portion observing lens 29' of a high power is inserted in the optical path of the observing optical system 8, the reduction lens 25 is inserted in the alignment optical system 5 in such a manner as to interlock with the insertion of the observing lens 29'. Then, since the incident angle $\theta_2$ of the ray of light Po' becomes large, the degree of conformity and nonconformity of the alignment target image i is increased when the anterior portion image Z is formed on the CCD 27 in its enlarged scale. And, when an anterior portion observing lens of a low power (not shown) is inserted in the observing optical system 8, the reduction lens 25 is retracted from the alignment optical system 5 in such a manner as to interlock with the insertion of the anterior portion observing lens of low power into the observing optical system 8. Then, since the incident angle $\theta_2$ of the ray of light Po' becomes small, the sensitivity of separation and conformity of the alignment target image i is lowered when the anterior portion image Z is formed CCD 27 in its reduced scale and the sensitivity of separation and conformity can be changed in accordance with the rough alignment and the fine alignment.

Although a plurality of embodiments have been described in the foregoing, the illuminating light for illuminating the anterior portion may be a visible light. In this case, the dichroic mirror 18 is of visible light half transmitting and infrared light half transmitting type, the dichroic mirror 21 is of visible light reflecting and infrared light transmitting type, the dichroic mirror 23 is of visible light reflecting and infrared light transmitting type, and the dichroic mirror 24 is of visible light half transmitting and infrared light transmitting type.

What is claimed is:

1. A noncontact type tonometer comprising:
   a nozzle for discharging fluid toward an eye to be tested, said nozzle aligned with an axis;
   an alignment target projecting optical system for projecting alignment target light toward the center of curvature of the cornea of the eye from a direction coaxial with said nozzel and for converging said alignment target light with an objective lens to form a virtual image at the center of curvature of the cornea; and
   an alignment light receiving optical system for reimaging the virtual image on a light receiving portion thereof, said alignment light receiving optical system comprising a means for splitting said alignment target light into a plurality of separated bundles of rays and means for guiding said plurality of separated bundles to said light receiving portion to reimage said virtual image by specular reflection from the cornea, thereby allowing the alignment of the tonometer to be verified.

2. The noncontact type tonometer of claim 1, wherein said light splitting means comprises a filter.

3. The noncontact type tonometer of claim 2, wherein said filter includes circular transmitting areas optically transparent to said alignment target light.

4. A noncontact type tonometer comprising:
   a nozzle having a tip for discharging fluid toward an eye to be tested, said nozzle disposed about an axis;
   an alignment target projecting optical system for projecting alignment target light toward the center of curvature of the cornea of the eye from a direction coaxial with said nozzle and for converging said alignment target light with an objective lens to form a virtual image at the center of curvature of the cornea;

an illuminating light source for illuminating the anterior portion of the eye;

an observing optical system for observing the anterior portion of the eye through the objective lens; and an alignment light receiving optical system for reimaging the virtual image on a light receiving portion, said alignment light receiving optical system comprising means for splitting said alignment target light into a plurality of separated bundles of rays and means for guiding said plurality of separated bundles to said light receiving portion to reimage said virtual image by specular reflection from the cornea, thereby allowing the alignment of the tonometer to be verified.

5. A noncontact type tonometer according to claim 4, wherein said alignment target light and an illuminating light from said illuminating light source are different wavelengths, said alignment target light being an infrared light and said illuminating light being either infrared light or visible light.

6. A noncontact type tonometer according to claim 4, wherein said observing optical system comprises means for switching between a low power and a high power.

7. A noncontact type tonometer according to claim 4, wherein said alignment light receiving optical system comprises a reduction lens means for reducing the power disposed between said light receiving portion and said light splitting means when a rough adjustment of a working distance from the apex of the cornea of the eye to the tip of said nozzle is performed.

8. A noncontact type tonometer according to claim 6, wherein said alignment light receiving optical system comprises a reduction lens means for reducing the power disposed between said light receiving portion and said light splitting means when a rough adjustment of a working distance from the apex of the cornea of the eye to the tip of said nozzle is performed, said reduction lens means being interlocked with said observing optical system to insert a reduction lens between said light receiving portion and said light splitting means when said observing optical system utilizes high power and retracted from between said light receiving portion and said light splitting means when said observing optical system utilizes low power.

9. A noncontact type tonometer according to claim 4, wherein said nozzle is placed coaxial with said objective lens.

10. A noncontact type tonometer according to claim 9, wherein a fixation mark light is projected toward the retina of the eye through said nozzle.

* * * * *